United States Patent
Shlepr et al.

[11] Patent Number: 6,140,652
[45] Date of Patent: Oct. 31, 2000

[54] DEVICE CONTAINING SAMPLE PREPARATION SITES FOR TRANSMISSION ELECTRON MICROSCOPIC ANALYSIS AND PROCESSES OF FORMATION AND USE

[75] Inventors: Mike G. Shlepr, Palm Bay; Jay J. Jeffreys, Indialantic, both of Fla.

[73] Assignee: Intersil Corporation, Palm Bay, Fla.

[21] Appl. No.: 09/150,429

[22] Filed: Sep. 9, 1998

[51] Int. Cl.[7] .................................................. G21K 5/08
[52] U.S. Cl. .......................... 250/440.11; 250/491.1; 428/141; 428/428; 428/450; 428/446
[58] Field of Search ................................ 428/426, 428, 428/446, 156, 450; 250/310, 311, 440.11, 491.1, 492.11

[56] References Cited

U.S. PATENT DOCUMENTS

| | | | |
|---|---|---|---|
| 5,367,171 | 11/1994 | Aoyama et al. | 250/443.1 |
| 5,440,123 | 8/1995 | Ikeda et al. | 250/307 |
| 5,572,026 | 11/1996 | Ikeda et al. | 250/307 |
| 5,821,544 | 10/1998 | Agustus et al. | 250/440.11 |
| 5,907,157 | 3/1999 | Yoshioka et al. | 250/492.2 |
| 5,935,870 | 8/1999 | Lee | 438/692 |
| 5,990,478 | 11/1999 | Liu | 250/307 |

OTHER PUBLICATIONS

C.J. Varker and L. H. Chang, "Preparation of Large–Area, Electron–Transparent Silicon Specimens by Anisotropic Etching", Solid State Technology, Apr. 1983, pp. 143 through 147.

David B. Williams, (David Bernard) 1949, Transmission Electron Microscopy: A Textbook for Materials Science, Chapter 1, "Materials–Microscopy" and Chapter 10, "Specimen Preparation" (No Month).

Jamie H. Rose and Richard Flutie, "Sample Preparation for Transmission Electron Microscopy Studies in Microelectronics", Digital Equipment Corporation, Northboro, MA 01532, pp. 13–1 through 13–7, Copyright 1990, ASM International, Metals Park, OH.

Primary Examiner—Timothy Speer
Assistant Examiner—Stephen Stein
Attorney, Agent, or Firm—Jaeckle Fleischmann & Mugel

[57] ABSTRACT

A device contains at least one sample preparation site for transmission electron microscopic (TEM) analysis. Included in the device is a first layer of silicon dioxide that serves as a substrate, a layer of silicon overlying the substrate, a second layer of silicon dioxide deposited on the silicon layer, and a continuous trench that circumscribes a sample preparation site for TEM analysis. The trench extends through the second layer of silicon dioxide and the layer of silicon; that portion extending through the silicon dioxide layer is wider than the portion through the silicon layer. In a process for forming a device containing at least one sample preparation site for TEM analysis, a layer of silicon is formed on a silicon dioxide substrate that is optionally attached to a silicon handle. A second layer of silicon dioxide is formed on the silicon layer, and a mask forming a continuous trench is etched in the second silicon dioxide layer. The trench is extended by retrograde etching through the layer of silicon. A portion of the second layer of silicon dioxide adjacent to the continuous trenches is removed, thereby widening the portion of the trench extending through the second silicon dioxide layer to a width greater than that of the portion through the silicon layer. The resulting trench circumscribes a sample preparation site for TEM analysis. A process for preparing a sample for TEM analysis entails the formation of a thin film of sample material on the second silicon dioxide layer of the described device.

16 Claims, 3 Drawing Sheets

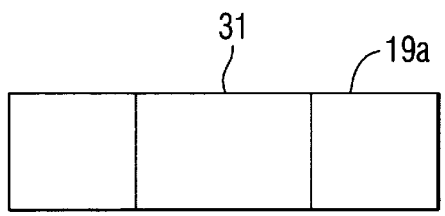
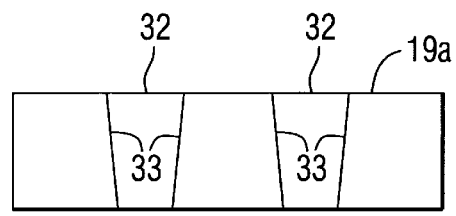
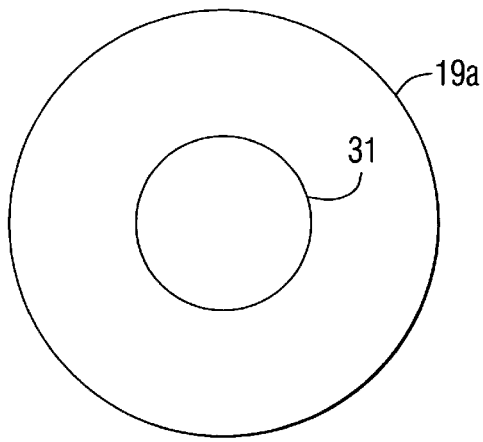
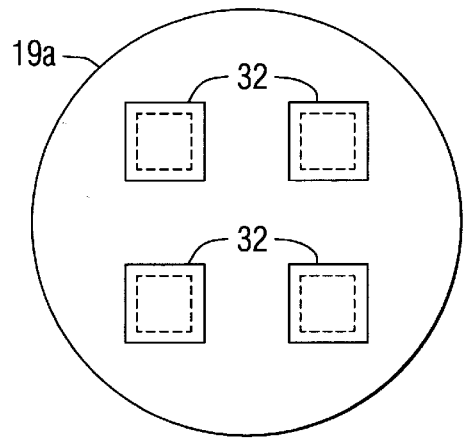
FIG. 3A
FIG. 3B
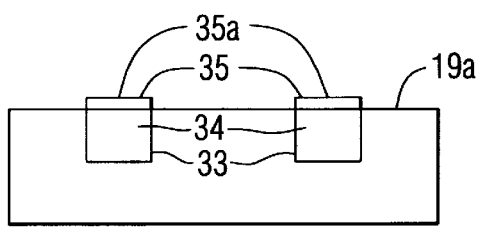
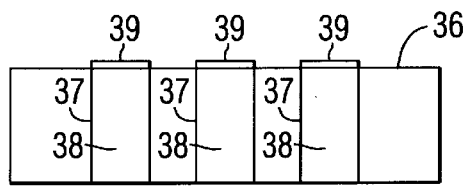
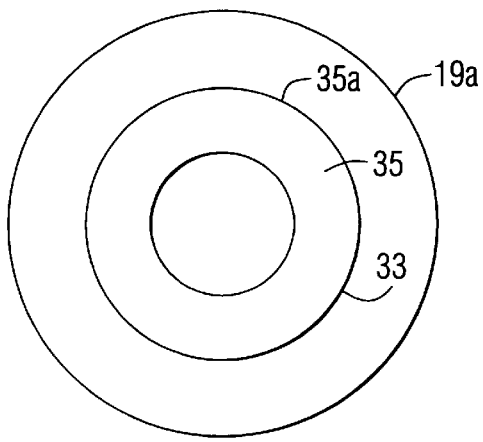
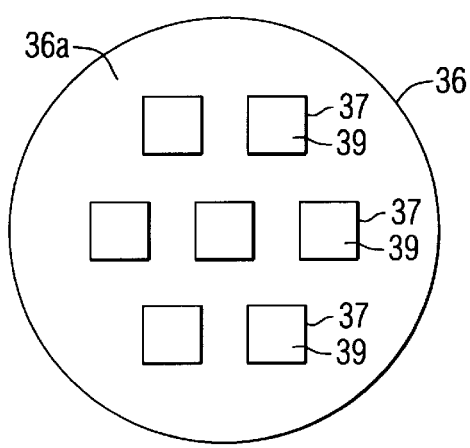
FIG. 3C
FIG. 3D

DEVICE CONTAINING SAMPLE PREPARATION SITES FOR TRANSMISSION ELECTRON MICROSCOPIC ANALYSIS AND PROCESSES OF FORMATION AND USE

FIELD OF THE INVENTION

The present invention is related to transmission electron microscopic (TEM) analysis and, more particularly, to a device containing a sample preparation site especially useful for, but not limited to, TEM analysis of deposited films, and to a process for forming and using the device.

BACKGROUND OF THE INVENTION

Transmission electron microscopy (TEM) is a technique that employs a beam of electrons to ascertain details at the atomic level of a sample of interest. Such samples can vary greatly in their physical properties, ranging from ductile metals to brittle ceramics.

The preparation of a sample for TEM analysis is typically an arduous, non-routine process because of the requirement that the sample be transparent to electrons. Thus, the sample must be extremely thin, less than 1 micrometer, preferably less than 500 nanometers, more preferably less than 100 nanometers. Consequently, a large part of TEM sample preparation has to do with the removal of unwanted material.

Transmission electron microscopes in current use typically require samples in the form of electron-transparent discs having a diameter of 3 millimeters. Various methods have been developed for constructing individual extremely thin discs; such methods include slicing, sawing, grinding, electropolishing, and ion milling. Techniques for TEM sample preparation are discussed in, for example, Williams and Carter, *Transmission Electron Microscopy: A Textbook for Materials Science*, 1996, Plenum Press, New York, pages 3–17 and 155–173, and Rose and Flutie, "Sample Preparation for Transmission Electron Microscopy Studies in Microelectronics" in *Microelectronics Failure Analysis*, 1990, ASM International, Metals Park, Ohio, pages 13-1 to 13-7, the disclosures of which are incorporated herein by reference.

Reducing the effort of TEM sample preparation has been a goal of many workers in the field. Varker and Chang, "Preparation of Large-area, Electron-Transparent Silicon Specimens by Anisotropic Etching" in *Solid State Technology*, April 1983, pages 143–146, describe thinning 48 millimeter windows of electron-transparent silicon over an entire wafer. However the resultant wafer is too fragile for further processing. Other workers have proposed depositing a thin film directly on TEM grids coated with a carbon support film. The deposited film is, however, not representative of the manufacturing process. Furthermore there is an unacceptable risk of contamination to the sample film and deposition equipment.

Thus, there remains a need for a convenient preparation of samples for TEM analysis that can be applied to a wide variety of materials and enables the simultaneous preparation of multiple samples. The present invention meets this need.

SUMMARY OF THE INVENTION

The present invention is directed to a device that contains at least one sample preparation site for transmission electron microscopic (TEM) analysis. Included in the device is a first layer of silicon dioxide that serves as a substrate, a layer of silicon overlying the substrate, a second layer of silicon dioxide deposited on the silicon layer, and a continuous trench that circumscribes a sample preparation site for TEM analysis. The trench extends through the second layer of silicon dioxide and the layer of silicon; that portion extending through the silicon dioxide layer is wider than the portion through the silicon layer.

Also in accordance with the present invention is a process for forming a device containing at least one sample preparation site for TEM analysis. A layer of silicon is formed on a silicon dioxide substrate that is optionally attached to a silicon handle. A second layer of silicon dioxide is formed on the silicon layer, and a mask forming a continuous trench is etched in the second silicon dioxide layer. The trench is extended by retrograde etching through the layer of silicon. A portion of the second layer of silicon dioxide adjacent to the continuous trenches is removed, thereby widening the portion of the trench extending through the second silicon dioxide layer to a width greater than that of the portion through the silicon layer. The resulting trench circumscribes a sample preparation site for TEM analysis.

Further in accordance with the present invention, a process for preparing a sample for TEM analysis entails the formation of a thin film of sample material on the second silicon dioxide layer of the described device. The process further includes adhering a TEM grid to the thin film of sample material and applying a wax sealant that forms a seal with the silicon layer of the device and encompasses the TEM grid, thin film, and a second layer of silicon dioxide. The substrate, silicon layer, and second silicon dioxide layer are etched away, and the wax sealant is removed by dissolution.

BRIEF DESCRIPTION OF THE DRAWINGS

FIGS. 3A–3D schematically depict variations in the device of the present invention.

DETAILED DESCRIPTION OF THE INVENTION

Figure 1B:
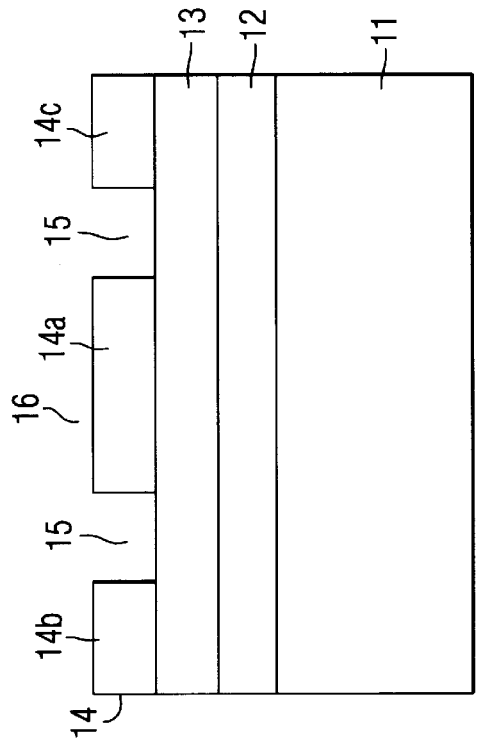
FIGS. 1A–1D schematically depict the formation of the device of the present invention.
Figure 1D:
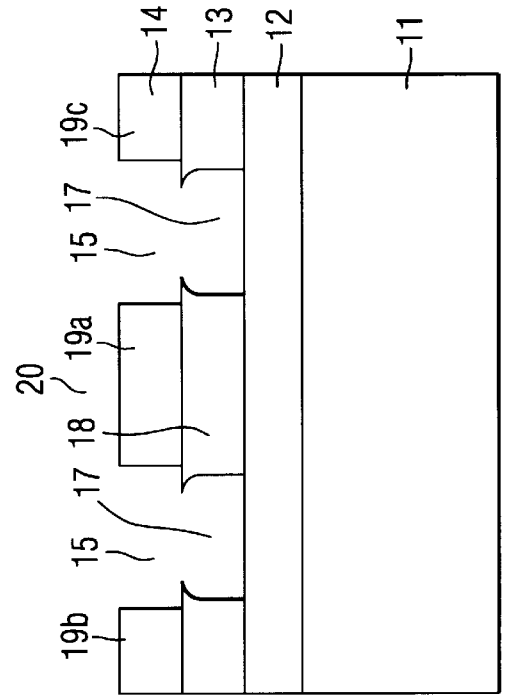
Figure 1A:
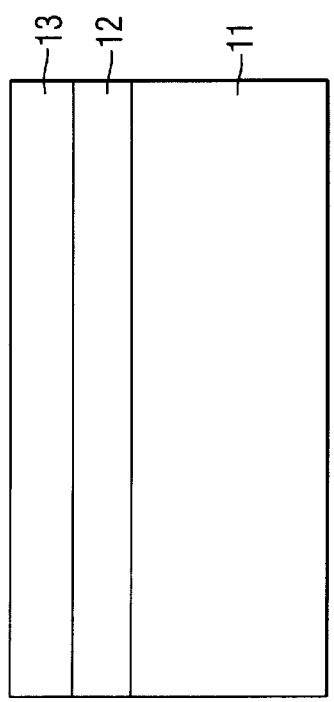

FIGS. 1A–D schematically depict the formation of a device containing a sample preparation site for TEM analysis. In FIG. 1A is shown a handle silicon layer 11 having a thickness typically of about 0.5 millimeter. On handle layer 11 is formed a substrate 12 comprising a first layer of silicon dioxide, whose thickness is about 1 to 2 micrometers. Bonded on substrate 12 is device silicon layer 13, also having a thickness of about 1 to 2 micrometers. The structure of FIG. 1A is a typical bonded silicon-on-insulator wafer where the device silicon has been chemomechanically polished to a thickness of about 1 to 2 micrometers. Alternatively, other materials having a thin silicon layer on an underlying substrate, such as silicon-on-sapphire or polysilicon on a glass plate, can be utilized.

As shown in FIG. 1B, a second silicon dioxide layer 14 is formed on silicon layer 13. Silicon dioxide layer 14 is etched by standard photolithography and anisotropic oxide etch techniques, thereby forming a continuous, preferably circular, trench first portion 15 extending through layer 14 and bounding unetched portion 14a. Following stripping of the photoresist, trench portion 15 and the unetched portions 14a, 14b and 14c of layer 14 constitute a hard mask 16.

Figure 1C:
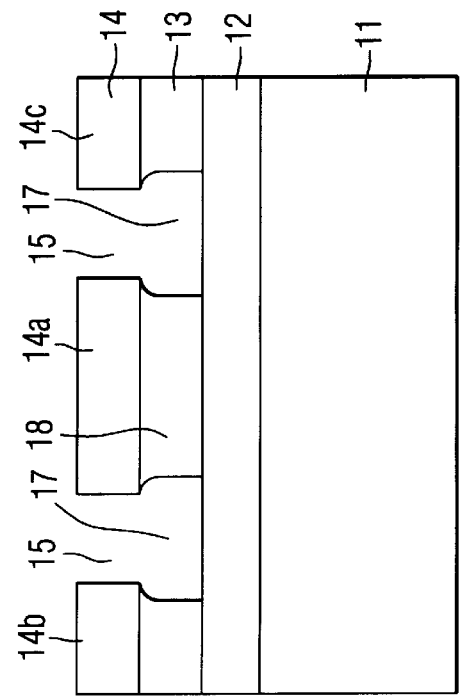

FIG. 1C depicts the retrograde etching, using a $SF_6/CF_4$ RIE silicon etch chemistry and mask 16 to define the areas to be etched through silicon layer 13, thereby forming a continuous, preferably circular, trench second portion 17 as an extension of trench first portion 15. As shown in FIG. 1C, the width of trench second portion 17 encircling silicon layer portion 18 is greater than that of trench first portion 15.

In FIG. 1D is shown the further etching by standard photolithography and anisotropic oxide etch techniques of silicon dioxide layer portions 14a, 14b, and 14c to produce corresponding smaller portions 19a, 19b, and 19c.

In the embodiment where continuous trench first and second portions 15 and 17, respectively, are circular, portions 18 and 19a are, of course, also circular, silicon layer portion 18 having a diameter larger than that of silicon dioxide layer portion 19a. Layer portions 18 and 19a encircled by trench portions 17 and 15, respectively, comprise a sample preparation site 20 for TEM analysis in device 101.

In a preferred embodiment of the invention, the etching of silicon dioxide layer 14 produces a circular portion 14a having a diameter of about 3.2 millimeters, and the retrograde etching of silicon layer 13 produces a circular portion 18 that is concentric with portion 14a and has a diameter of about 3.0 millimeters. Subsequent etching of portion 14a yields circular portion 19a, whose diameter is about 2.8 millimeters. This preferred embodiment is especially suitable for use with typical transmission electron microscopes, which require samples in the form of discs having a diameter of 3 millimeters.

Figure 2A:
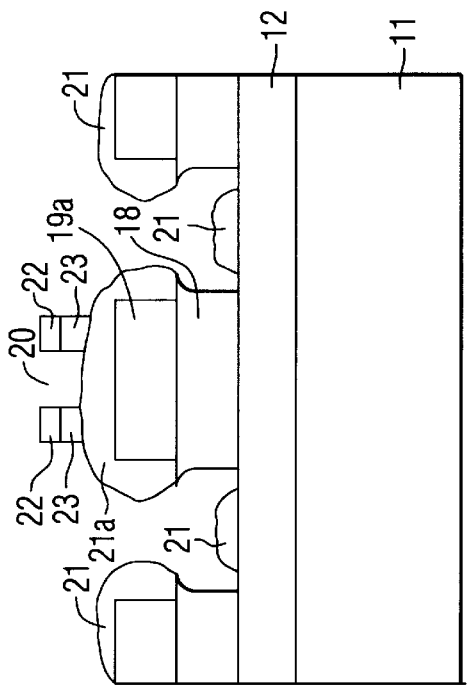
FIGS. 2A–2D schematically depict the preparation of a sample for TEM analysis using the device of the present invention.

FIGS. 2A–2D schematically depict the preparation of a sample for TEM analysis using device 101. In FIG. 2A is shown the deposition of a thin film 21 on device 101. Thin film 21, having a thickness preferably of about 50 nanometers to about 500 nanometers, can be deposited by a wide variety of deposition techniques. Thin film 21 may be any material of interest for TEM analysis, such as, for example, a crystalline material that can be a metal or metal alloy, a semiconductor, or an insulator. Thin film 21 may be further processed to include delineation, deposition of additional materials, and nondestructive measurements of material properties.

Figure 2B:
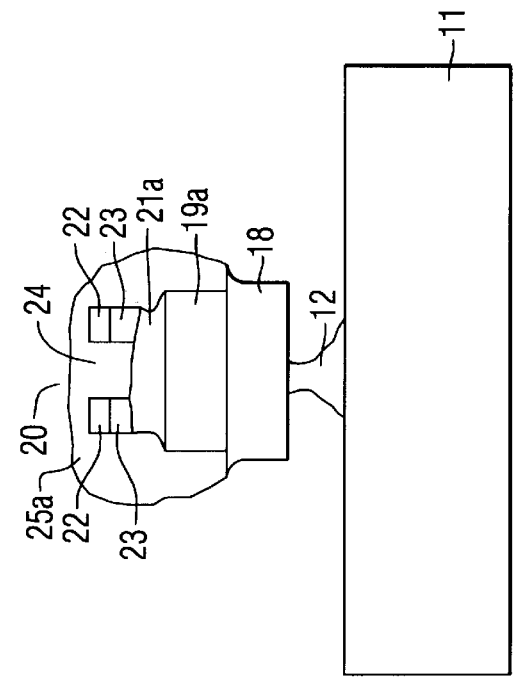

FIG. 2B depicts the attachment of TEM grid 22 to thin film portion 21a that is deposited on a sample preparation site 20. TEM grid 22 can be affixed to thin film portion 21a using, for example, an epoxy adhesive 23.

Figure 2C:
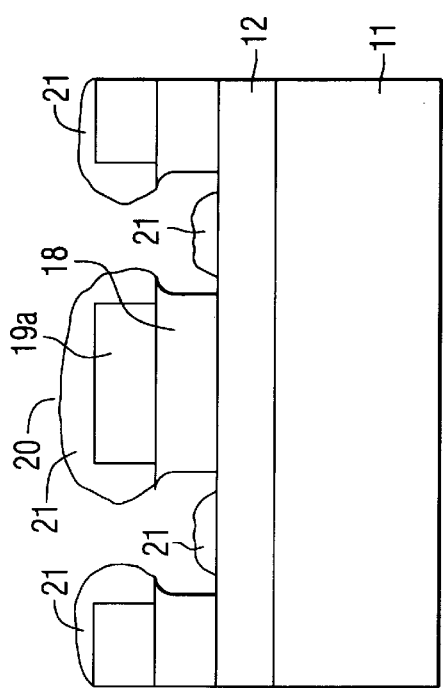

FIG. 2C shows the filling of hole 24 of TEM grid 22 with wax sealant 25 and the removal of thin film portion 21 not located on sample preparation site 20 by etching with a fluid etchant. An aluminum thin film 21, for example, can be removed with phosphoric acid.

Figure 2D:
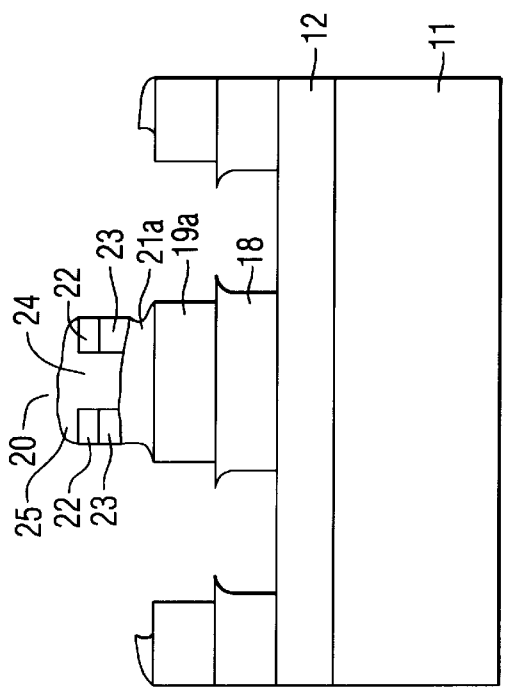

In FIG. 2D is shown the application of additional wax sealant 25a, which encloses TEM grid 22, epoxy adhesive 23, thin film portion 21a, and silicon dioxide layer portion 19a, and forms a seal with silicon layer portion 18.

Silicon dioxide substrate 12 is removed by lateral etching resulting from immersion of the device 101 in hydrofluoric acid. The device 101 remains in the hydrofluoric acid bath until the sample preparation site 20 is completely undercut and thereby freed from the device 101, i.e., sample preparation site 20 is "lifted-off" device 101. For example, a 2 mm×3 mm sample preparation site 20 was can be undercut and freed from device 101 in about 2 hours using 49% HF heated to 45–50° C. This procedure allows all the sample preparation sites 20 to be removed from device 101. Following this undercut and lift-off procedure, the silicon layer portion 18 is removed using a $CF_4$ plasma, KOH, or $HF/HNO_3$. Silicon dioxide layer portion 19a is then removed or partially removed by hydrofluoric acid, care being taken to avoid overetching. Dissolution of wax sealant 25a produces a sample suitable for TEM analysis that comprises thin film portion 21a affixed to TEM grid 22 by epoxy adhesive 23.

The device of the present invention allows the examination of thin films deposited on the materials other than silicon dioxide. For example, the nucleation and reaction of metal deposited on silicon can be studied using a structure whose top view and cross-sectional view through the center are schematically depicted in FIG. 3A. The circularly shaped second layer of silicon dioxide 19a is provided with a single aperture 31 that extends to the underlying silicon layer 18. The area of aperture 31 can be varied to accomodate the compromise between thin film 21 support and TEM analysis area. Metals can be deposited on and allowed to react with underlying silicon layer 18.

The structure shown in FIG. 3B provides for a similar deposition of the thin film on both silicon dioxide and silicon. In this instance, second silicon dioxide layer 19a is provided with a plurality of apertures 32, preferably with sloped sidewalls 33 for step-cover. The plurality of apertures 32 allows for multiple TEM sample examination sites.

In FIG. 3C is schematically depicted, in a top view and a cross-sectional view through the center, a variant of the device of the invention in which circularly shaped second layer 19a is provided with a circular trench 33 that is concentric with layer 19a and extends into but not through layer 19a. Trench 33 is filled with polysilicon 34, which is then polished to form a smooth surface with the surrounding surface of silicon dioxide layer 19a. A thin layer 35, about 100 angstroms thick, of silicon dioxide is thermally grown on polished polysilicon 34. Following removal of silicon layer portion 18, layer 19a is removed with hydrofluoric acid to provide a rigid, single-hole support ring 35a for fragile thin films 21. The internal diameter of the support ring 35a can, once again, be varied to accommodate the compromise between thin film 21 support and TEM analysis area.

FIG. 3D schematically depicts, in a top view and a cross-sectional view through the center, a variant of the device of the invention in which circularly shaped second silicon dioxide layer 19a is replaced with circularly shaped silicon nitride layer 36. Silicon nitride layer 36, which can have a thickness of about 1 micrometer to 2 micrometers, is provided with a grid array of apertures 37 extending through layer 36 to underlying silicon layer 18 (cf. FIG. 1D). Apertures 37 are filled with silicon 38, which can be polysilicon or epitaxially deposited silicon. Silicon 38 is polished to form a smooth surface with the surrounding surface of silicon nitride layer 36. A thin layer 39 of silicon dioxide, about 100 angstroms thick, is thermally grown on polished silicon 38. After the previously described undercut and lift-off procedure, the silicon 38 of this variant is etched simultaneously with silicon layer 18. The resulting structure is a rigid support mesh 36a that is particularly suitable for delineated thin films 21 such as, for example, integrated circuit interconnects.

Parts List 11 handle silicon layer
12 silicon dioxide substrate
13 device silicon layer
14 silicon dioxide layer
14a silicon dioxide layer portion 14b silicon dioxide layer portion
14c silicon dioxide layer portion
15 trench portion
16 hard mask
17 trench portion
18 silicon layer portion
19a silicon dioxide layer portion
19b silicon dioxide layer portion
19c silicon dioxide layer portion
20 sample preparation site
21 deposited thin film
21a thin film portion
22 TEM grid
23 epoxy adhesive
24 TEM grid hole
25 wax sealant
25a additional wax sealant
31 aperture
32 plurality of apertures
33 circular trench
34 polysilicon
35 silicon dioxide layer
35a support ring
36 silicon nitride layer
36a support mesh
37 plurality of apertures
38 polished silicon layer
39 silicon dioxide layer The invention has been described in detail for the purpose of illustration, but it is understood that such detail is solely for that purpose, and variation can be made therein by those skilled in the art without departing from the spirit and scope of the invention, which is defined by the following claims.

What is claimed:

1. A device containing at least one sample preparation site for transmission electron microscopic (TEM) analysis, said device comprising:

a substrate comprising a first layer of silicon dioxide;

a layer of silicon overlying the substrate;

a second layer of silicon dioxide deposited on said layer of silicon; and a continuous trench circumscribing a sample preparation site for TEM analysis, said trench comprising a first portion extending through said second layer of silicon dioxide and a second portion extending through said layer of silicon, wherein said first portion of said trench is wider than said second portion of said trench.

2. The device of claim 1 further comprising:

a handle layer of silicon underlying said substrate.

3. The device of claim 1 wherein said substrate has a thickness of about 1 micrometer to 2 micrometers.

4. The device of claim 1 wherein said layer of silicon has a thickness of about 1 micrometer to 2 micrometers.

5. The device of claim 5 wherein said first and said second portions of said continuous trench each has a circular shape.

6. The device of claim 5 wherein said layer of silicon and said second layer of silicon dioxide circumscribed by, respectively, said second and said first portions of said trench each has a circular shape concentric with one another, the layer of silicon having a diameter greater than the diameter of the second layer of silicon dioxide.

7. The device of claim 6 wherein said layer of silicon has a diameter of about 3.2 millimeters and said second layer of silicon dioxide has a diameter of about 2.8 millimeters.

8. The device of claim 6 wherein said second layer of silicon dioxide contains at least one aperture extending through it.

9. The device of claim 8 wherein said aperture has a circular cross-section and is centered in said circularly shaped second layer of silicon dioxide.

10. The device of claim 8 wherein said circularly second layer of silicon dioxide contains a plurality of apertures in a grid array, each said aperture having a square cross-section.

11. The device of claim 6 wherein said circularly shaped layer of silicon dioxide includes a concentric trench extending into but not through said layer, said trench being filled with polysilicon.

12. The device of claim 11 further comprising a layer of silicon dioxide on said silicon in said trench.

13. The device of claim 6 wherein said circularly shaped second layer of silicon dioxide is replaced by a circularly shaped layer of silicon nitride.

14. The device of claim 13 wherein said layer of silicon nitride contains at least one aperture extending through it.

15. The device of claim 14 wherein said apertures through said silicon nitride layer is filled with polysilicon or epitaxially deposited silicon.

16. The device of claim 1 comprising a multiplicity of sample preparation sites for TEM analysis.

* * * * *